(12) United States Patent
Maxik (10) Patent No.: US 11,202,919 B2
(45) Date of Patent: Dec. 21, 2021

(54) WAVELENGTH CONVERTING THERAPEUTIC TREATMENT AND ASSOCIATED METHODS

(71) Applicant: Lighting Science Group Corporation, Cocoa Beach, FL (US)

(72) Inventor: Fredric S. Maxik, Cocoa Beach, FL (US)

(73) Assignee: Healthe, Inc., Orlando, FL (US)

( * ) Notice: Subject to any disclaimer, the term of this patent is extended or adjusted under 35 U.S.C. 154(b) by 486 days.

(21) Appl. No.: 15/474,412

(22) Filed: Mar. 30, 2017

(65) Prior Publication Data

US 2018/0280719 A1    Oct. 4, 2018

(51) Int. Cl.
*A61N 5/06* (2006.01)
*A61F 13/02* (2006.01)
*A61F 13/00* (2006.01)

(52) U.S. Cl.
CPC ...... *A61N 5/0616* (2013.01); *A61F 13/00034* (2013.01); *A61F 13/00063* (2013.01); *A61F 13/023* (2013.01); *A61F 13/0206* (2013.01); *A61N 5/062* (2013.01); *A61N 5/0625* (2013.01); *A61N 2005/0645* (2013.01); *A61N 2005/0659* (2013.01); *A61N 2005/0663* (2013.01)

(58) Field of Classification Search
CPC ........................ A61N 5/0616; A61F 13/00034
USPC .......................................................... 607/88
See application file for complete search history.

(56) References Cited

U.S. PATENT DOCUMENTS

| 6,051,747 | A | * | 4/2000 | Lindqvist ............ A61F 13/0203 602/41 |
| 2002/0018632 | A1 | * | 2/2002 | Pelka ..................... B82Y 10/00 385/130 |
| 2007/0083175 | A1 | * | 4/2007 | Van Himbergen .......................... A61F 13/15203 604/367 |
| 2010/0318161 | A1 | | 12/2010 | Brawn |
| 2014/0277297 | A1 | | 9/2014 | Harris et al. |

FOREIGN PATENT DOCUMENTS

| EP | 2422844 A1 * | 2/2012 | ............... A61N 5/06 |
| WO | 2002009630 A1 | 2/2002 | |
| WO | 20100123592 A2 | 10/2010 | |

OTHER PUBLICATIONS

European Patent Office International Searching Authority, International Search Report and Written Opinion, PCT/US2018/025385, dated Jun. 22, 2018.

(Continued)

*Primary Examiner* — Nadia A Mahmood
(74) *Attorney, Agent, or Firm* — Mark R. Malek; Widerman Malek, PL (57) ABSTRACT

A wavelength converting bandage including a substrate with an external surface and an internal surface. The wavelength converting bandage includes a plurality of quantum dots, each quantum dot individually sized to emit light within a wavelength range of 613 nm to 846 nm, defined as converted light. The wavelength converting bandage includes at least a portion of the substrate constructed to adhere to skin. The substrate may receive ambient light from the environment on the external surface and may emit converted light toward the skin.

15 Claims, 4 Drawing Sheets

(56) References Cited

OTHER PUBLICATIONS

Bungart, et al., "Nanoparticle-Emitted Light Attenuates Amyloid-β-Induced Superoxide and Inflammation in Astrocytes", Jan. 2014, National Institute of Health, <https://www.ncbi.nlm.nih.gov/pmc/articles/PMC3895489/pdf/nihms537934.pdf>.
De Abreu Chaves, et al., "Effects of Low-Power Light Therapy on Wound Healing: Laser X LED", Jul.-Aug. 2014, Anais Brasileiros De Dermatologia, Official publication of the Brazilian Society of Dermatology, <https://www.ncbi.nlm.nih.gov/pmc/articles/PMC4148276/>.
Kim, et al., "Is Light-Emitting Diode Photography (LED-LLLT) Really Effective?", 2009, Journal of Biomedical Science, <http://www.ncbi.nlm.nih.gov/pmc/articles/PMC3799034/pdf/islsm-20-205.pdf>.

\* cited by examiner

WAVELENGTH CONVERTING THERAPEUTIC TREATMENT AND ASSOCIATED METHODS

FIELD OF THE INVENTION

The present invention relates to skin care treatment and, more particularly, to skincare treatment that allows for the use of ambient light and converting wavelengths thereof.

BACKGROUND

For years, healthcare professionals have debated the issue as to whether a bandage may promote or inhibit healing of an abrasion or skin wound. Traditional thought was that leaving an abrasion uncovered allows ambient light and air through to the wound thereby allowing it to scab and heal quicker. Modern studies have shown that exposing an abrasion to open air may in fact cause it to scab quicker, however, the scabbing itself may inhibit skin regeneration and overall healing of the wound. Scabbing and slower skin regeneration can mean scarring as well.

Modern techniques in skin care have included covering an abrasion with a bandage, and in some cases applying a thin layer of antibiotic cream. The antibiotic not only prevents infection, but slows the scabbing process by moisturizing the skin. This allows for the skin to regenerate before scabbing. Additionally, the bandage provides a protective layer that would otherwise naturally occur from scabbing.

However, the modern approach often excludes the healing ability of light. If an abrasion is covered with a bandage or dressing, light does not make its way through to the skin. Traditional bandages and dressings, even those with clear securing members, include an occlusive pad or gauze that absorbs fluid, but also blocks out light. Furthermore, the bandages with clear securing members may allow ambient light through to the skin surrounding an abrasion, but don't allow for light to reach the abrasion. If light does happen to reach the abrasion, it is pure ambient light that includes the entire wavelength spectrum, which dilutes the type of light proven to assist in skin regeneration.

A division of the United States National Library of Medicine (NLM) named the National Center for Biotechnology Information (NCBI) has published several articles citing studies demonstrating the skin healing benefits of light therapy. See, *Effects of low-power light therapy on wound healing: Laser x LED; Is light-emitting diode phototherapy (LED-LLLT) really effective?; Nanoparticle-emitted Light Attenuates Amyloid-β-induced Superoxide and Inflammation in Astrocytes*; These articles make it clear that light produced within a wavelength range of 613 to 846 nm, or near red to infrared light, is optimal for energy absorption within the skin and optimal for skin regeneration. Therefore, there is a need in the art for an invention that protects the skin while simultaneously delivering enhanced therapeutic light to an abrasion and surrounding skin. Slightly warming the skin in the process may also provide comfort as an added benefit.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to skin care treatment, comfort and maintenance including treatment and protection of abrasions. The present application describes a wavelength converting bandage including a substrate with an external surface and an internal surface. The wavelength converting bandage may include a plurality of quantum dots, each quantum dot being individually sized to emit light within a wavelength range of 613 nm to 846 nm, defined as converted light. The wavelength converting bandage may include at least a portion of the substrate constructed to adhere to skin. The substrate may receive ambient light from the environment on the external surface and may emit converted light toward the skin.

In some embodiments, the wavelength converting bandage may include quantum dots contained within a suspension medium that is configured to coat at least a portion of the substrate internal surface.

Furthermore, the substrate may be configured to increase in temperature when exposed to ambient light and the radii of each of the quantum dots may be configured to have a maximum axis dimension within a range of 2.8 nm to 3.2 nm. The substrate may comprise translucent material configured to permit at least one of ambient light and converted light to propagate therethrough in a direction toward the skin. The substrate may comprise a treatment section and an adhesive section.

In some embodiments, the wavelength converting bandage may further comprise a first cover layer and a second cover layer wherein the substrate may be encapsulated between the first cover layer and the second cover layer. In this embodiment, the first cover layer may comprise an absorbent pad. The second cover layer may be encapsulated within a raised medial portion of the wavelength converting bandage. Additionally, the absorbent pad may comprise spaced apart holes configured to permit converted light from the second cover layer to propagate therethrough.

Another embodiment of the wavelength converting bandage may include a first cover layer and a substrate, defined as a second cover layer. The substrate may include an external surface and an internal surface as well as a plurality of quantum dots sized to emit light, defined as converted light, ranging from red to infrared. At least a portion of the first cover layer may be configured to adhere to skin. Furthermore, the second cover layer may be configured to receive ambient light from the environment on the external surface and the internal surface may be configured to emit converted light toward the skin. The converted light may be emitted within a range of 613 nm to 846 nm. Furthermore, the radii of each of the quantum dots may be configured to have a maximum axis dimension within a range of 2.8 nm to 3.2 nm. A variation of this embodiment may include a third cover layer wherein the second cover layer may be encased between the first cover layer and the third cover layer. The second cover layer may be encapsulated within a raised medial portion of the wavelength converting bandage.

Like the other embodiments, at least a portion of the first cover layer may comprise an absorbent pad with spaced apart holes configured to permit converted light to propagate therethrough. These holes may be symmetrically sized and spaced squares. Furthermore, at least a portion of the first cover layer may comprise translucent material configured to permit the converted light to propagate therethrough in a direction toward the skin.

Yet another embodiment may be a wavelength converting bandage comprising a first cover layer and a substrate, defined as a second cover layer. The second cover layer may have an external surface and an internal surface. It may also have a plurality of quantum dots with radii sized within a range of 2.8 nm to 3.2 nm and configured to emit light, defined as converted light, within a wavelength range of 613 nm to 846 nm. There may also be a third cover layer.

The second cover layer may be encapsulated between the first cover layer and the third cover layer and at least a portion of the first cover layer may be configured to adhere to skin. In some embodiments, the second cover layer may be encapsulated within a raised medial portion of the wavelength converting bandage. The second cover layer may be configured to receive ambient light from the environment on the external surface and the internal surface may be configured to emit converted light toward the skin.

The wavelength converting bandage itself may be any number of shapes including polygonal, oval, or circular. Furthermore, the quantum dots may be sized to emit converted light ranging from red to infrared and the second cover layer may be configured to increase in temperature when exposed to ambient light.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Figure 1:
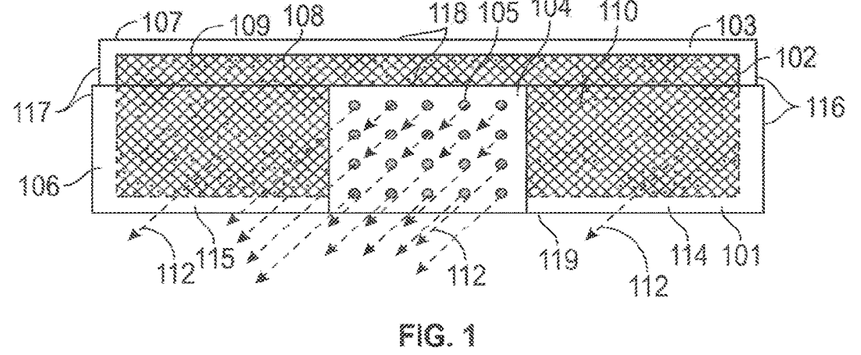
FIG. 1 is a perspective view of a wavelength converting bandage according to an embodiment of the present invention.

Referring to FIG. 1, the wavelength converting bandage 100 may include a first cover layer 101, a second cover layer 102, and a third cover layer 103, together forming a single bandage. The wavelength converting bandage 100 may include a bandage first end 116 and a bandage second end 117 and may include a bandage top 118 and a bandage bottom 119. Likewise, the wavelength converting bandage 100 may include a bandage application surface 106 and a bandage rear surface 107.

The first cover layer 101 may be made of translucent or transparent material constructed in a manner to allow light to pass therethrough. The first cover layer 101 may include a medial pad 104 located at its center, thereby bisecting the first cover layer 101 into a pair of end segments 114, 115 on opposing sides of the medial pad 104. In some embodiments, the end segments 114, 115 may be equally dimensioned, and in other embodiments they may be unequally dimensioned. Furthermore, while in the present invention the end segments have a generally rectangular configuration, any geometric configuration is contemplated and included within the scope of the invention, including all regular and irregular polygons. Each of the end segments 114, 115 may include adhesive material on the bandage application surface 106 sufficient to adhere the wavelength converting bandage 100 to a patient. The medial pad 104 may include propagation holes 105 dimensioned to allow light from the second cover layer 102 to propagate therethrough. By way of non-limiting example, the propagation holes 105 may be circular, oval, square, rectangular, or polygonal in shape.

The second cover layer 102 may be a substrate located between the first cover layer 101 and the third cover layer 103. The second cover layer 102 may be made of translucent or transparent material constructed in a manner to allow light to pass therethrough. The second cover layer 102 may include a plurality of quantum dots 110. The plurality of quantum dots 110 may be configured to emit light within a range from 613 nm to 846 nm. Additionally, the plurality of quantum dots 110 may be configured to have radii within a range from 2.8 nm to 3.2 nm. The second cover layer 102 may include an internal surface 108 facing the first cover layer 101 and an external surface 109 facing the third cover layer 103.

In some embodiments, the second cover layer 102 may have generally the same geometric configuration/shape and, in some embodiments, may be generally coextensive with the first and third cover layers 101, 103. In the present embodiment, the second cover layer 102 may span from the bandage first end 116 to the opposing bandage second end 117. The second cover layer 102 may also span from the bandage top 118 to the bandage bottom 119. In other embodiments, the second cover layer 102 may be similar in shape, but slightly smaller than the first and third cover layers 101, 103 thereby leaving a nominal gap between the edges of the second cover layer 102 and the bandage first and second ends 116, 117 and the bandage top and bottom 118, 119.

The third cover layer 103 may have generally the same geometric configuration/shape and, in some embodiments, be generally coextensive with the first cover layer 101. The third cover layer 103 may be made of translucent or transparent material constructed in a manner to allow light to pass therethrough. In some embodiments, the third cover layer 103 may be integrally formed with the first and second cover layer 101, 102 to form a monolithic bandage. In other embodiments, a monolithic bandage may be formed from the third cover layer 103 being joined to the second cover layer 102 by any means or method known in the art, including adhesion, gluing, epoxying, cementing, fastening, and the like. Likewise, the second cover layer 102 may be joined to the first cover layer 101 by any means or method mentioned above. In yet other embodiments, a monolithic bandage may be formed from the first cover layer 101 being joined to the third cover layer 103 around an inside perimeter of both, by any means or method mentioned above. In this embodiment, the inner perimeter may be formed by the nominal distance between the edges of a smaller second cover layer 102 along with the bandage first and second ends 116, 117 and the bandage top and bottom 118, 119. In this embodiment, the second cover layer may or may not be joined to either or both of the first and third cover layers 101, 103.

Use of the wavelength converting bandage 100 depicted in FIG. 1 may include removing it from protective packaging. A patient with an abrasion may place the medial pad 104 overtop the abrasion and may secure the wavelength converting bandage 100 by adhering the bandage application surface 106 of the first and second ends 116, 117 to the patient's skin. Therefore, the bandage application surface 106 may face the patient's skin and the bandage rear surface 107 may be exposed to the environment surrounding the wavelength converting bandage 100. Likewise, the internal surface 108 of the second cover layer 102 may face the patient's skin and the external surface 109 of the second cover layer 102 may face the bandage rear surface 107 and the environment. Since the third cover layer 103 may be made of transparent or translucent material, the quantum dots 110 within the second cover layer 102 may be exposed to ambient light form the environment. Once exposed to ambient light, the quantum dots 110 may slightly increase in temperature and may emit light, defined as converted light 112, within a wavelength range of 613 to 846 nm, alternatively characterized as being within the near red to infrared spectrum. The converted light 112 emitted by the quantum dots 110 may then propagate through the propagation holes 105 of the medial pad 104 as well as through the transparent or translucent material of the first cover layer 101. As indicated in FIG. 1, the converted light 112 may propagate through the bandage application surface 106 toward the patient's skin to irradiate the patient's skin and facilitate healing the abrasion.

Additionally, converted light 112 may propagate through the end segments 114, 115 to deliver the converted light 112 to the skin surrounding the abrasion. The converted light 112 may also propagate through the propagation holes 105 of the medial pad 104 to deliver converted light 112 directly to the abrasion. Therefore, the wavelength converting bandage 100 may deliver healing, converted light 112 to the patient's abrasion and surrounding skin while simultaneously warming the patient's skin for comfort.

Figure 2:
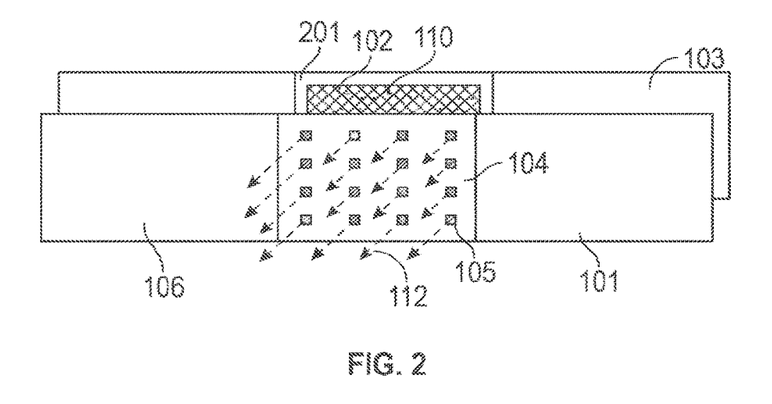
FIG. 2 is a perspective view of a wavelength converting bandage according to an embodiment of the present invention.

FIG. 2 depicts another embodiment where the second cover layer 102 may have generally the same geometric configuration/shape and be generally coextensive with the medial pad 104. In this embodiment, the end segments 114, 115 of the first and third cover layer 101, 103 may or may not be made of transparent or translucent material. In this embodiment, the translucent or transparent material may be a cover layer window 201 within a medial section of the third cover layer 103 that overlays the second cover layer 102. Here, the cover layer window 201 may allow for the quantum dots 110 to be exposed to ambient light, propagate through the medial pad 104 via the propagation holes 105, and direct converted light 112 through to the patient's abrasion opposing the bandage application surface 106 of the medial pad 104. The propagation holes in FIG. 2 are square, but may include any shape and dimension necessary to allow enough converted light 112 to pass therethrough for healing.

In some embodiments, the medial pad 104 may be replaced entirely with the cover layer window 201. In this embodiment, the second cover layer 102 may be overlain by a transparent or translucent cover layer window 201 on both the first and third cover layer 101, 103. With this embodiment, there are no propagation holes 105, since converted light 112 propagates through the cover layer window 201 of the first cover layer 101 toward the abrasion.

Figure 3:
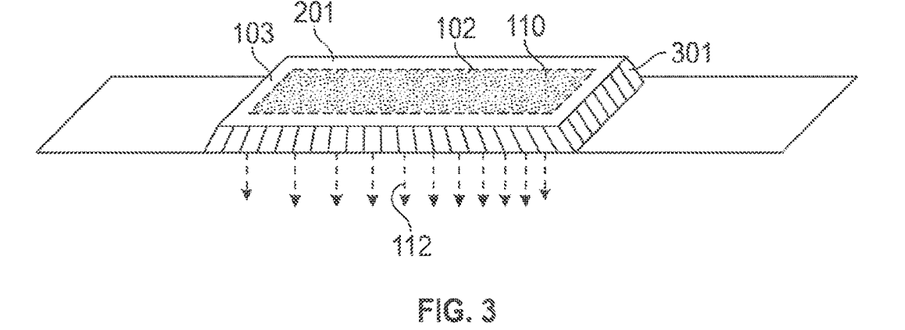
FIG. 3 is a perspective view of a wavelength converting bandage according to an embodiment of the invention.

FIG. 3 depicts an embodiment similar to that of FIG. 2 whereby the second cover layer 102 may be located between a medial portion of the first and the third cover layer 101, 103. However, in the present embodiment, the second cover layer 102 may be located within a raised medial section 301 of the wavelength converting bandage 100. The end segments 114, 115 of the first and third cover layer 101, 103 may or may not be made of transparent or translucent material. In this embodiment, the translucent or transparent material may also be a cover layer window 201 within a medial portion of the third cover layer 103 that overlays the second cover layer 102. Here, the cover layer window 201 may enable the exposure of the quantum dots 110 to ambient light. The quantum dots 110 may then emit converted light through the medial pad 104 via the propagation holes 105 and direct the converted light 112 through to the patient's abrasion. Additionally, like FIG. 2, in some embodiments the medial pad 104 may be replaced by a transparent or translucent cover layer window 201 on both the first and third cover layer 101, 103. The use of a cover layer window instead of a medial pad 104 would mean there are no propagation holes 105, since converted light 112 propagates through the entire window of the first cover layer 101 toward the abrasion.

The raised medial section 301 of FIG. 3 may also provide more options as to the composition of the second cover layer 102 by providing more volume between the first and third cover layers 101, 103. In some embodiments, the second cover layer may include a colloidal suspension or suspension medium (both terms aggregated hereinafter as suspension medium) whereby the quantum dots 110 are suspended therein. In other embodiments, the suspension medium may be a coating applied to at least a portion of the second cover layer 102 substrate including its internal and external surfaces 108, 109.

Figure 4:
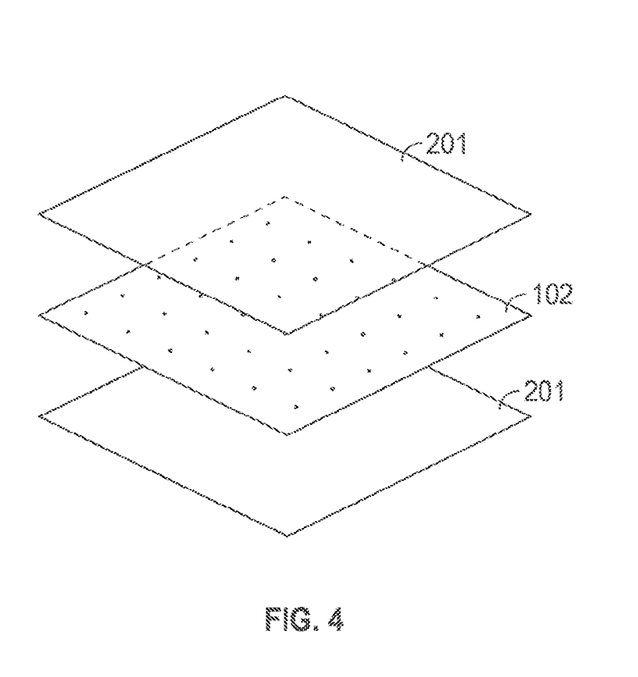
FIG. 4 is an exploded view of a wavelength converting bandage.

FIG. 4 depicts another embodiment of a wavelength converting bandage comprising, and in some embodiments, consisting of two cover layer windows 201 encapsulating a second cover layer 102 with quantum dots 110. In this embodiment, at least one surface of a cover layer window 201 is coated with an adhesive on its bandage application surface 106 in order to adhere the wavelength converting bandage 100 to a patient's skin. FIG. 4 also demonstrates that the wavelength converting bandage 100 itself may be any shape and size including square and any other regular or irregular polygon, circle, ellipse, oval, and the like.

Figure 5:
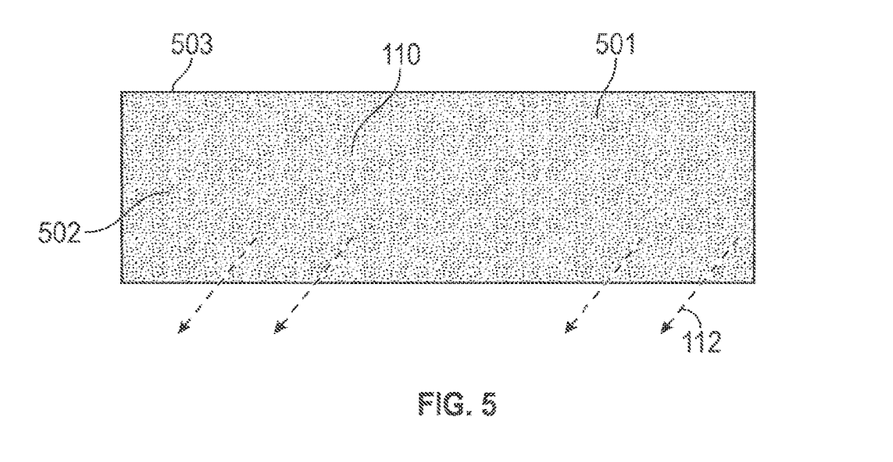
FIG. 5 is a bottom view of another embodiment of the wavelength converting bandage.

FIG. 5 depicts an embodiment of the wavelength converting bandage 100 whereby there is a single substrate 501 comprising a single layer with an internal surface 502 and external surface 503. Here, the quantum dots 110 may be located on and/or within the single substrate 501 and the internal surface 502 may be coated with an adhesive. The internal surface 502 of the single substrate 501 may adhere directly to a patient's skin over an abrasion. In this embodiment, the quantum dots 110 may receive ambient light and emit converted light 112 onto a patient's skin to warm it and facilitate healing. As with all the embodiments, the quantum dots 110 may be individually sized with radii in a range between 2.8 nm and 3.2 nm to emit light within a wavelength range of 613 nm to 846 nm and deliver a colored light between near red and infrared.

Figure 6:
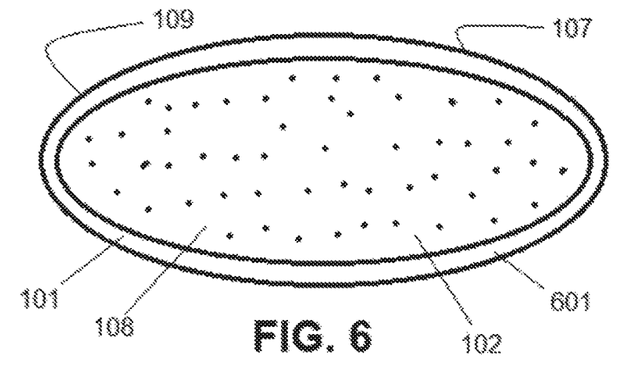
FIG. 6 is a bottom view of another embodiment of the wavelength converting bandage.

FIG. 6 depicts an embodiment of the wavelength converting bandage 100 where there may be two layers comprising, or, in some embodiments, consisting of a first cover layer 101 and a second cover layer 102 substrate. In this embodiment, the first cover layer 101 may include the bandage application surface 106 and may be made of translucent or transparent material constructed to allow light to pass therethrough. The second cover layer 102 may overlay the first cover layer 101 with its internal surface 108 facing the first cover layer 101 and its external surface 109 comprising the bandage rear surface 107. In some embodiments, there may be an adhesive laced perimeter 601 used to adhere the wavelength converting bandage 100 to a patient's skin. In other embodiments, the entire bandage application surface 106 of the first cover layer 101 may be laced with an adhesive used to adhere the wavelength converting bandage 100 to a patient's skin.

The application and functionality of the wavelength converting bandage 100 embodied in FIGS. 2-6 are essentially the same as FIG. 1. A bandage application surface 106 may be applied to a patient's skin overtop an abrasion. The quantum dots 110 may be exposed to ambient light to slightly increase in temperature as well as produce converted light 112. The converted light 112 may be directed to one or both of the abrasion site and the surrounding skin to promote healing. The increased temperature of the quantum dots 110 may provide patient comfort by either warming the skin directly or warming the wavelength converting bandage 100 to indirectly warm the skin.

Figure 7:
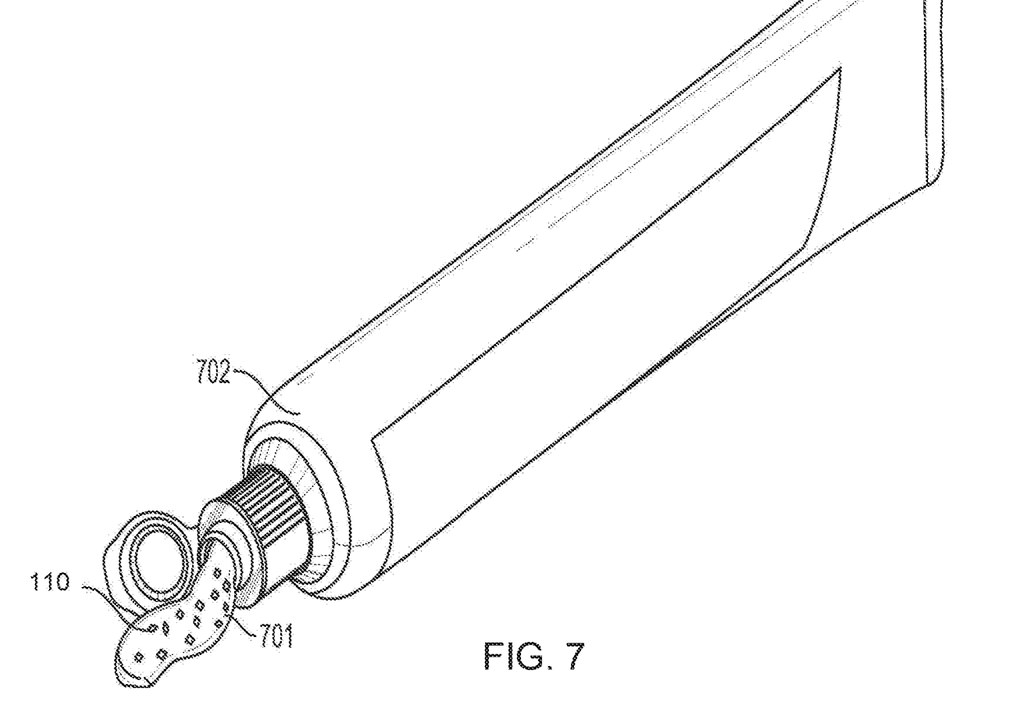
FIG. 7 is a perspective view of a suspension medium containing quantum dots.

FIG. 7 depicts a quantum dot suspension medium 701 whereby the quantum dots 110 may be suspended therein. The suspension medium 701 may be any transparent or translucent matter capable of suspending the quantum dots 110 on a temporary or permanent basis. In some embodiments, the quantum dot suspension medium 701 may be applied directly onto a patient's skin. The quantum dots 110 themselves may then be directly touching or in close proximity to the patient's skin. This enables warmth and converted light 112 to be directed to the patient's skin offering comfort and healing principles. In other embodiments, as mentioned hereinabove, the suspension medium 701 may be used as a coating on other components of the wavelength converting bandage 100 thereby delivering warmth and healing in bandage form. The suspension medium 701 may be dispensed from a container 702 configured to dispense the suspension medium 701, the container 702 being any such container known in the art capable of such dispensing.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus, the scope of the invention should be determined by the appended claims and their legal equivalents, and not by the examples given.

That which is claimed is:

1. A wavelength converting bandage comprising:
    a first cover layer comprising an absorbent pad having a thickness wherein the absorbent pad comprises spaced apart holes that extend through an entirety of the thickness of the absorbent pad;
    a second cover layer; and
    a substrate encapsulated between the first cover layer and the second cover layer, comprising:
        an external surface;
        an internal surface; and
        a plurality of quantum dots, each quantum dot individually sized to emit light within a wavelength range of 613 nm to 846 nm, defined as converted light;
    wherein at least a portion of the substrate is configured to adhere to skin;
    wherein the substrate is configured to receive ambient light from an environment surrounding the bandage on the external surface;
    wherein the internal surface is configured to emit converted light toward the skin; and
    wherein the spaced apart holes of the absorbent pad are configured to permit converted light from the substrate to propagate therethrough.

2. The wavelength converting bandage of claim 1 wherein the quantum dots are contained within a suspension medium configured to coat at least a portion of the internal surface of the substrate.

3. The wavelength converting bandage of claim 1 wherein the substrate is configured to increase in temperature when exposed to ambient light.

4. The wavelength converting bandage of claim 1 wherein a radii of each of the quantum dots are configured to have a maximum axis dimension within a range of 2.8 nm to 3.2 nm.

5. The wavelength converting bandage of claim 1 wherein the substrate comprises translucent material configured to permit at least one of ambient light and converted light to propagate therethrough in a direction toward the skin.

6. A wavelength converting bandage comprising:
    a first cover layer comprising an absorbent pad having a thickness wherein the absorbent pad comprises spaced apart holes that extend through an entirety of the thickness of the absorbent pad; and
    a substrate, defined as a second cover layer, the substrate comprising:
        an external surface;
        an internal surface; and
        a plurality of quantum dots sized to emit light, defined as converted light, ranging from red to infrared;
    wherein at least a portion of the first cover layer is configured to adhere to skin;
    wherein the second cover layer is configured to receive ambient light from an environment surrounding the bandage on the external surface and the internal surface is configured to emit converted light toward the skin; and
    wherein the spaced apart holes of the absorbent pad are configured to permit converted light from the substrate to propagate therethrough.

7. The wavelength converting bandage of claim 6 wherein the converted light is emitted within a range of 613 nm to 846 nm.

8. The wavelength converting bandage of claim 6 wherein a radii of each of the quantum dots are configured to have a maximum axis dimension within a range of 2.8 nm to 3.2 nm.

9. The wavelength converting bandage of claim 6 further comprising a third cover layer; and wherein the second cover layer is encased between the first cover layer and the third cover layer.

10. The wavelength converting bandage of claim 6 wherein the second cover layer is encapsulated within a raised medial portion of the wavelength converting bandage.

11. The wavelength converting bandage of claim 6 wherein the spaced apart holes are symmetrically sized and spaced squares.

12. The wavelength converting bandage of claim 6 wherein at least a portion of the first cover layer comprises translucent material configured to permit the converted light to propagate therethrough in a direction toward the skin.

13. A wavelength converting bandage comprising:
    a first cover layer comprising an absorbent pad having a thickness wherein the absorbent pad comprises spaced apart holes that extend through an entirety of the thickness of the absorbent pad;
    a substrate, defined as a second cover layer, comprising:
        an external surface;
        an internal surface; and
        a plurality of quantum dots with radii sized within a range of 2.8 nm to 3.2 nm and configured to emit light, defined as converted light, within a wavelength range of 613 nm to 846 nm; and
    a third cover layer;
    wherein the second cover layer is encapsulated between the first cover layer and the third cover layer;
    wherein at least a portion of the first cover layer is configured to adhere to skin;
    wherein the second cover layer is configured to receive ambient light from an environment surrounding the bandage on the external surface and the internal surface is configured to emit converted light toward the skin; and
    wherein the spaced apart holes of the absorbent pad are configured to permit converted light from the substrate to propagate therethrough.

14. The wavelength converting bandage of claim 13 wherein the second cover layer is encapsulated within a raised medial portion of the wavelength converting bandage.

15. The wavelength converting bandage of claim 13 wherein the quantum dots are sized to emit converted light ranging from red to infrared; and wherein the second cover layer is configured to increase in temperature when exposed to ambient light.

* * * * *